US011766208B2

(12) United States Patent
Hetling et al.

(10) Patent No.: US 11,766,208 B2
(45) Date of Patent: *Sep. 26, 2023

(54) DEVICE FOR ELECTROPHYSIOLOGICAL RECORDING FROM THE EYE

(71) Applicant: Retmap, Inc., Grayslake, IL (US)

(72) Inventors: John R. Hetling, Dyer, IN (US); Safa Rahmani, Northbrook, IL (US); Tamas Ban, Grayslake, IL (US)

(73) Assignee: RETMAP, INC., Grayslake, IL (US)

( * ) Notice: Subject to any disclaimer, the term of this patent is extended or adjusted under 35 U.S.C. 154(b) by 39 days.

This patent is subject to a terminal disclaimer.

(21) Appl. No.: 17/188,130

(22) Filed: Mar. 1, 2021

(65) Prior Publication Data

US 2021/0219905 A1     Jul. 22, 2021

Related U.S. Application Data

(63) Continuation of application No. 16/132,257, filed on Sep. 14, 2018, now Pat. No. 10,952,630, which is a continuation of application No. 15/407,450, filed on Jan. 17, 2017, now abandoned, which is a continuation of application No. 14/338,640, filed on Jul. 23, 2014, now abandoned.

(60) Provisional application No. 61/857,674, filed on Jul. 23, 2013.

(51) Int. Cl.
*A61B 5/398*     (2021.01)
*A61B 5/00*      (2006.01)

(52) U.S. Cl.
CPC .......... *A61B 5/398* (2021.01); *A61B 5/6821* (2013.01)

(58) Field of Classification Search
CPC ...... A61B 5/398; A61B 5/6821; A61B 5/0496
USPC .......................................... 351/291
See application file for complete search history.

(56) References Cited

U.S. PATENT DOCUMENTS

| | | | |
|---|---|---|---|
| 3,001,441 A | 9/1961 | Frederick | |
| 3,929,124 A | 12/1975 | Yabonski et al. | |
| 5,032,020 A | 7/1991 | Robert | |
| 8,326,935 B2 | 12/2012 | Wu | |

(Continued)

FOREIGN PATENT DOCUMENTS

WO     2013/124141 A1     8/2013

OTHER PUBLICATIONS

PET (polyethylene terepththalate), Designerdata, retrieved May 6, 2020 from internet, URL: https://designerdata.nl/materials/plastics/thermo-plastics/polyethylene-terephthalate, 3 pages.

(Continued)

*Primary Examiner* — George G. King
(74) *Attorney, Agent, or Firm* — Perkins Coie LLP (57) ABSTRACT

The present disclosure provides electroretinography devices configured to detect biopotential signals from an eye of a subject. In some embodiments, the device is configured to prevent the subject's eyelids from closing over the device when placed in contact with the anterior surface of the subject's eye. In some embodiments, the device has a Young's modulus of no more than about 50 MPa. In some embodiments, the device includes a diffusing or refracting element configured to scatter, focus or diverge incident light. In other embodiments, the device includes a void through which incident light can enter the subject's eye without passing through any portion of the device.

12 Claims, 10 Drawing Sheets (56) References Cited

U.S. PATENT DOCUMENTS

| | | |
|---|---|---|
| 9,026,189 B2 | 5/2015 | Garcia et al. |
| 10,952,630 B2 * | 3/2021 | Hetling ................ A61B 5/6821 |
| 2008/0294066 A1 | 11/2008 | Detling et al. |
| 2014/0200424 A1 | 7/2014 | Etzkorn et al. |
| 2014/0371565 A1 * | 12/2014 | Glasser ................ A61B 5/6821 |
| | | 600/383 |

OTHER PUBLICATIONS

MIT's Material Property Database, 2004, http://wwwmit.edu/~6.777/matprops/pdms.htm.

Lehman, "Overview of Glass Properties," (2003).

Burian et al., A Speculum Contact Lens Electrode for Electroretinography, Electroencephalography and Clinical Neurophysiology, vol. 6, pp. 509-511 (1954).

* cited by examiner

DEVICE FOR ELECTROPHYSIOLOGICAL RECORDING FROM THE EYE

PRIORITY CLAIM

The present application is a continuation of U.S. patent application Ser. No. 16/132,257 filed Sep. 14, 2018, which is a continuation of U.S. patent application Ser. No. 15/407,450 filed on Jan. 17, 2017, which is a continuation of U.S. patent application Ser. No. 14/338,640, filed on Jul. 23, 2014, which claims priority to U.S. Provisional patent application Ser. No. 61/857,674, filed on Jul. 23, 2013, the disclosures of which are incorporated herein by reference in their entireties.

BACKGROUND

The retina is the thin sheet of neural tissue that lines the inside of the eye, and which is responsible for converting the light that enters the eye into visual information that is then passed to the brain in the form of nerve impulses. Electroretinography (ERG) is the process of recording the bioelectric response of the retina in response to a visual stimulus, such as a brief flash of light. The response that is recorded when performing electroretinography is a voltage versus time waveform that can be analyzed to reveal a great deal of information about the physiology and health of the retina. ERG recording is therefore a commonly employed technique in vision science and ophthalmology. For instance, in ophthalmology, ERG recording can be used to diagnose a disease that affects the retina, such as glaucoma, or to monitor the effects of a treatment strategy aimed at a halting or reversing the damage caused by a retinal disease. ERG recording is non-invasive and is routinely performed in human subjects and animals such as mice, rats and cats.

ERG recording is accomplished by placing a recording electrode in gentle contact with the cornea, and then presenting a visual stimulus to the subject. The recording electrode can take one of several different forms.

Current reusable electroretinography devices can be expensive, scarce in the market, difficult to clean for reuse, uncomfortable for the subject, difficult to insert on the eye, and pose a risk of corneal abrasion due to the stiff materials used for construction. Current disposable electroretinography devices are typically highly unstable on the eye and produce inconsistent signals. Improved electroretinography devices are needed.

SUMMARY

The present disclosure provides electroretinography devices having the stability of a reusable device with the convenience of a disposable device formed primarily from a flexible, non-abrasive material to enhance subject comfort and safety. In some embodiments, the electroretinography device includes an electrode configured to contact the surface of a subject's eye. In some embodiments, a method of recording electroretinographic data includes contacting the surface of a subject's eye with an electrode housed in an electroretinography device disclosed herein.

In some embodiments, the present disclosure provides an electroretinography device comprising an ocular portion configured to detect a biopotential signal from an eye of a subject, the ocular portion including a proximal portion configured to be placed in contact with an anterior surface of the eye, a distal portion including at least one side wall, and a conductive element housed in the ocular portion; and a signal relay operatively connected to the conductive element and configured to transmit the biopotential signal from the conductive element to a signal processor.

Additional embodiments of the present technology may comprise the combination of one or more of the features described above, as well as variations of each feature that will be apparent to those of ordinary skill in the art based on the descriptions and figures included herein.

BRIEF DESCRIPTION OF THE DRAWINGS

Many aspects of the present technology can be better understood with reference to the following drawings. The relative dimensions in the drawings may be to scale with respect to some embodiments. With respect to other embodiments, the drawings may not be to scale. For ease of reference, throughout this disclosure identical reference numbers may be used to identify identical or at least generally similar or analogous components or features.

These and other embodiments of the present technology are described in further detail below.

DETAILED DESCRIPTION

The present disclosure generally provides electroretinography devices configured to detect a biopotential signal from an eye of a subject or a portion thereof (e.g., the retina) and transmit same to a processor. In some embodiments, the electroretinography device includes an ocular portion including a conductive element and a signal relay operatively connecting the conductive element and a signal processor.

A person of ordinary skill in the art will understand that embodiments of the present technology can have components and/or procedures in addition to those shown or described herein, and that these and other embodiments can be without several of the components and/or procedures shown or described herein without deviating from the present technology. The headings provided herein are for convenience only.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Generally, unless the context indicates otherwise, the terms "distal" and "proximal" within this disclosure reference a position or direction with respect to a subject's eye. "Distal" or "distally" therefore refer to a position distant from or in a direction away from the subject's eye, while the terms "proximal" and "proximally" refer to a position near or in a direction toward the subject's eye.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Figure 1A:
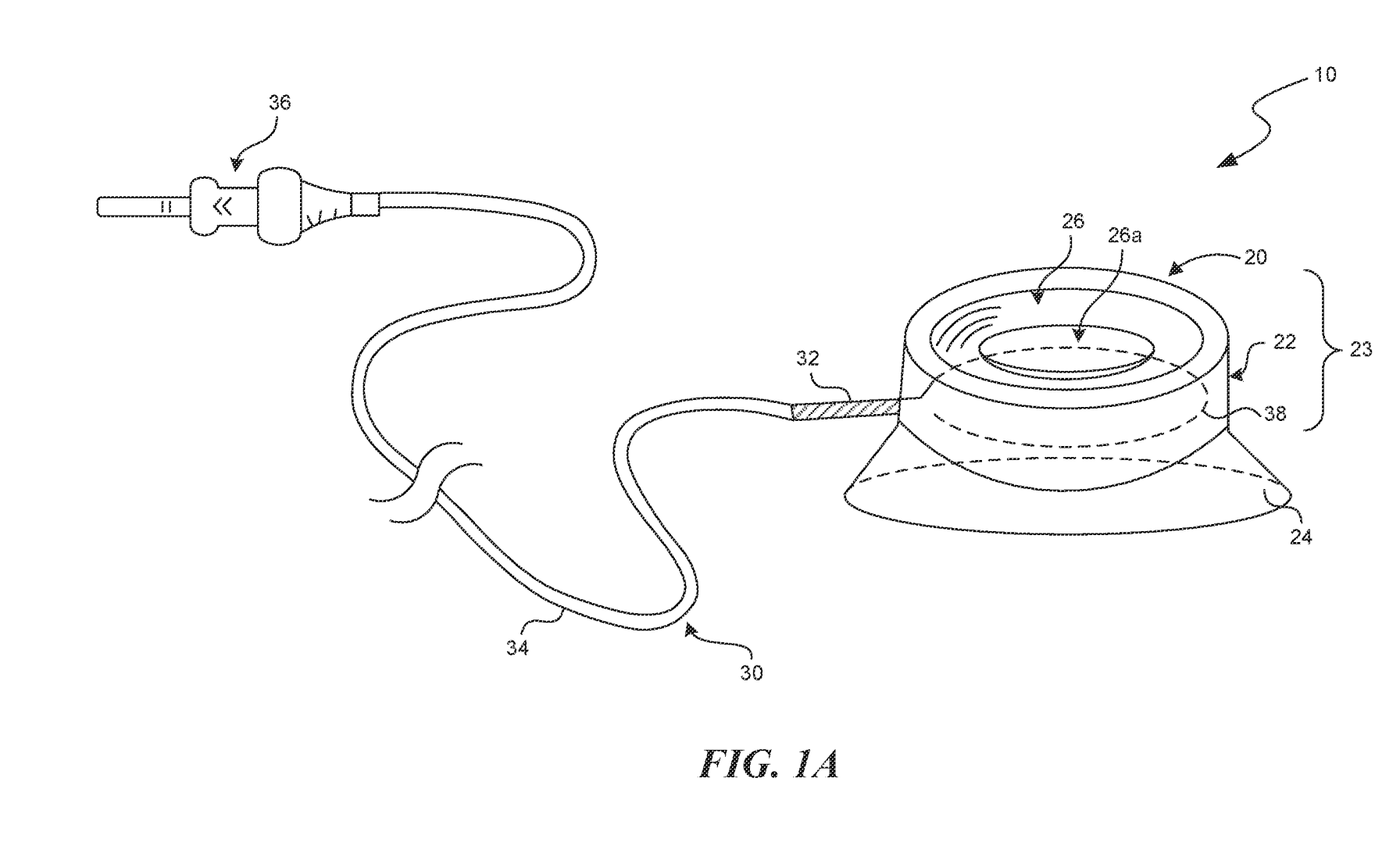
FIG. 1A is a perspective view of an electroretinography device configured according to one embodiment of the present technology.

Referring now to FIG. 1A, an electroretinography device 10 configured according to one embodiment of the present disclosure comprises an ocular portion 20 configured to be placed in contact with an anterior surface of a subject's eye, a conductive element 38 retained at least partially within the ocular portion 20, and a signal relay 30 configured to transmit an electrical signal from the conductive element 38 to a processor (not shown). In some embodiments, the signal relay 30 includes one or more wires 34 operatively connected to the conductive element 38, for example by a flexible shield 32. The signal relay 30 is configured to operatively connect to a signal processor (not shown), and therefore the signal relay 30 may include any suitable connector 36 compatible with the signal processor to be used.

Figure 1B:
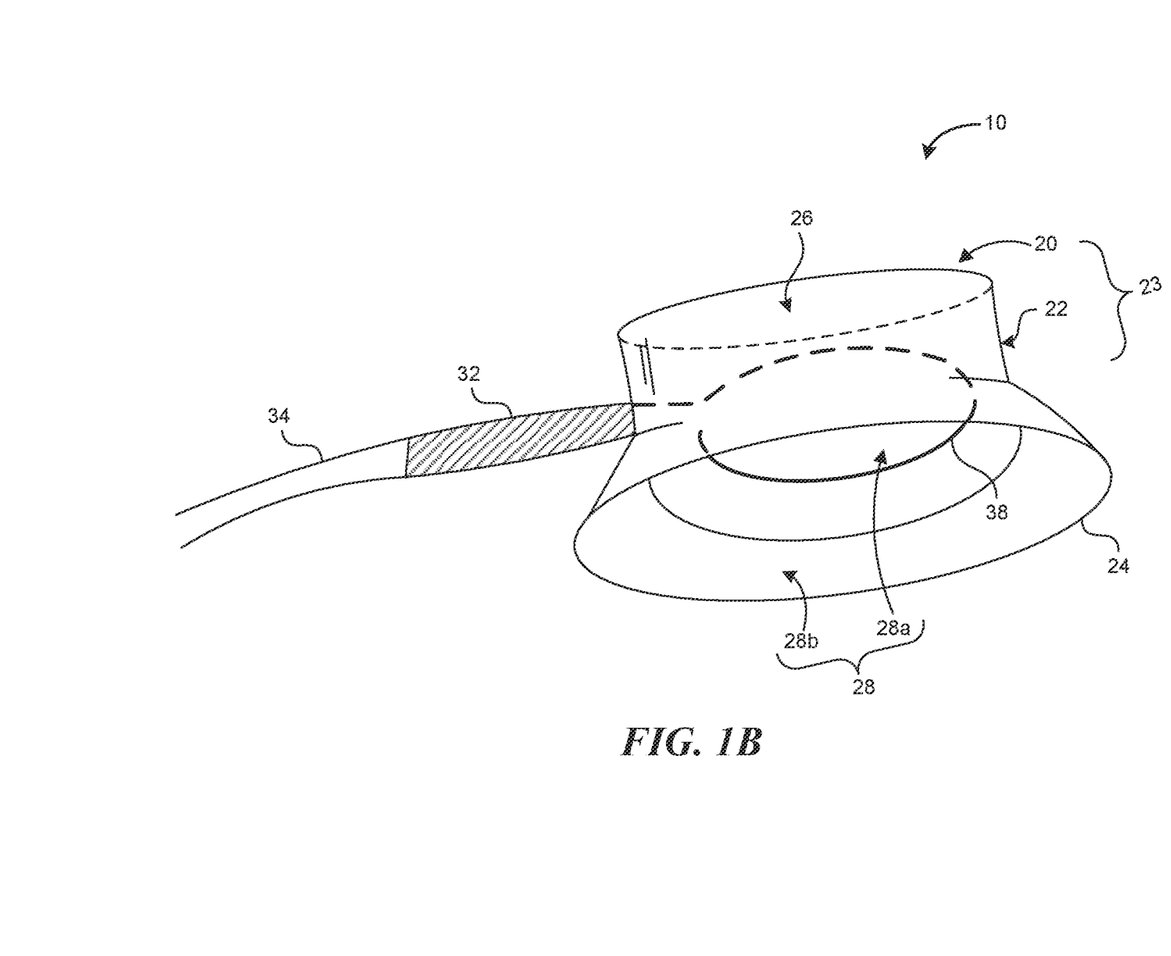
FIG. 1B is a perspective view of a portion of an electroretinography device configured according to another embodiment of the present technology as viewed from the proximal side.

Referring now to FIGS. 1A and 1B collectively, the ocular portion 20 includes a proximal portion 24 shaped to conform to the anterior surface of the subject's eye, including the cornea and/or the sclera. For example, the proximal surface 28 may include a curved shape, such as a concave shape, that substantially conforms to the anterior surface of a subject's eye. The ocular portion 20 may also include a distal portion 23 including one or more side walls 22. In some embodiments, the side wall(s) 22 are configured to stop one or more eyelids from sliding over the ocular portion 20 when in position on the anterior surface of the subject's eye. In some embodiments, the distal portion 23 includes a single side wall 22, and thus comprises a continuously curved cross-sectional profile, such as a circular cross-sectional profile, an oval cross-sectional profile, an ellipsoid cross-sectional profile, or any other rounded cross-sectional profile. In other embodiments, the distal portion has a polygonal cross-sectional profile, such as a triangular cross-sectional profile, a quadrilateral cross-sectional profile, a pentagonal cross-sectional profile, a hexagonal cross-sectional profile, a heptagonal cross-sectional profile, an octagonal cross-sectional profile, a nonagonal cross-sectional profile, a decagonal cross-sectional profile, or any other polygonal cross-sectional profile. In some embodiments, the distal portion 23 includes a cross-sectional profile including more than one curved segment and more than one straight segment.

Referring to FIG. 1A specifically, in some embodiments the ocular portion 20 may include a void 26a (e.g., a gap, hole, passage, channel, etc.) extending through the ocular portion 20 to allow incident light to pass through the ocular portion 20. The void 26a may be incorporated before, during or after formation of the ocular portion 20. For example, in some embodiments the void 26a is formed in the ocular portion 20 as part of a molding step. In other embodiments, the void 26a is formed in the ocular portion 20 after a molding step, for example by drilling or milling the void 26a into a molded ocular portion 20. In other embodiments, such as that shown in FIG. 1B for example, the ocular portion 20 may include a distal portion 23 that does not include a void. In such embodiments, the distal portion 23 may include a distal surface 26 having any suitable shape (e.g., contour), such as flat or substantially flat.

The proximal portion 28 may include one or two distinct contours to enable the ocular portion 20 to securely contact the anterior surface of the subject's eye. In some embodiments, the proximal portion 28 includes a single contour, for example that is complementary or substantially complementary to the curvature of at least a portion of the cornea. In other embodiments, such as that shown in FIG. 1B for example, the proximal portion 28 may include a first proximal surface 28a having a curvature that is complementary or substantially complementary to the curvature of at least a portion of the cornea, and a second proximal surface 28b having a curvature that is complementary or substantially complementary to the curvature of at least a portion of the sclera.

The ocular portion 20 may be formed of any suitable material that is biocompatible and transparent or translucent. In some embodiments, the material is flexible to reduce (e.g., minimize) the risk of mechanical abrasion to the anterior surface of the eye and/or the eyelids when the device is positioned on the subject's eye. In some embodiments, the material has a Young's modulus of elasticity of no more than about 50 mega-Pascals (50 MPa). In some embodiments, the materials comprise a component commonly used in the manufacture of soft contact lenses. In some embodiments, the material comprises, consists essentially of, or consists of polydimethylsiloxane ("PDMS"), which has a Young's modulus of elasticity of about 0.05 MPa to about 4.0 MPa.

The ocular portion 20 may be formed by any suitable fabrication techniques depending on the type of material(s) selected for the ocular portion 20. For example, the ocular portion 20 may be molded (e.g., injection molded) when the ocular portion 20 is formed predominantly of PDMS.

The conductive element 38 includes one or more wires configured to detect a biopotential signal from the subject's eye, for example from the retina. Any suitable electrically conductive material may be used to form the conductive element 38. For example and without limitation, the conductive element 38 may comprise, consist essentially of, or consist of stainless steel, gold, platinum, a conductive hydrogel, a conductive polymer, a conductive silicone, a doped silicon, a conductive saline, or combinations thereof. The conductive element 38 is housed at least partially in the ocular portion 20. For example, the conductive element 38 can be included at least partially within the distal portion 23, at least partially within the proximal portion 24, or at least partially in both, so long as the conductive element 38 is in electrical connectivity with the biopotential signals produced by the subject's eye.

The conductive element 38 can be configured to form any suitable shape, such as a curved shape or a polygon. In some embodiments, the conductive element 38 forms a shape such as a loop (e.g., a discontinuous loop such as that shown in FIG. 16). The conductive element 38 can be incorporated into the device 10 before, during or after formation of the ocular portion 20. For example, in some embodiments the conductive element 38 is placed into a mold before the material used to form the ocular portion is added to the mold. In other embodiments, the conductive element 38 is added to the ocular portion 20 after a molding step.

Figure 2:
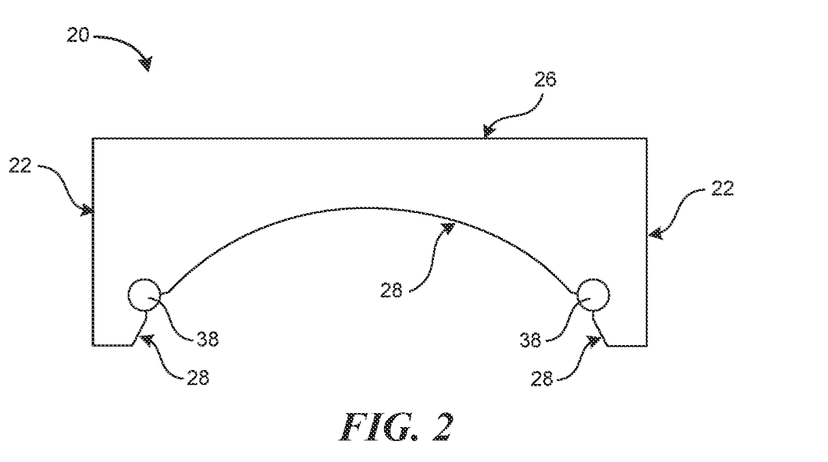
FIG. 2 is a cross sectional view through one embodiment of an electroretinography device configured in accordance with the present technology.

As shown in FIG. 2, one embodiment of the ocular portion 20 includes a distal surface 26, at least one side wall 22, and a proximal surface 28 which is curved to conform to the corneal surface of the subject's eye. The conductive element 38 is positioned within the ocular portion 20 such that the conductive element 38 is at least partially exposed through the proximal surface 28.

Figure 3:
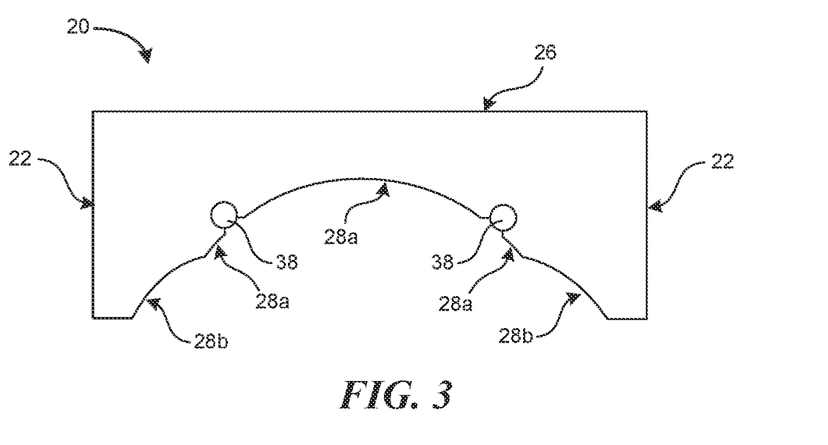
FIG. 3 is a cross sectional view through another embodiment of an electroretinography device configured in accordance with the present technology.
Figure 4:
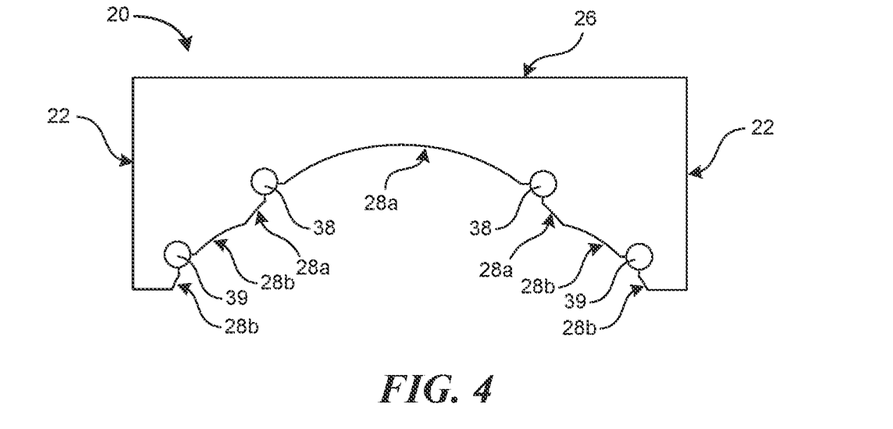
FIG. 4 is a cross sectional view through another embodiment of an electroretinography device configured in accordance with the present technology.

In some embodiments, such as that shown in FIG. 3, the ocular portion 20 includes a distal surface 26, at least one sidewall 22, a conductive element 38, a first proximal surface 28a configured to conform to the cornea of a subject's eye, and a second proximal surface 28b configured to conform to the sclera of the subject's eye. The conductive element may be positioned at any suitable location of the ocular portion 20. As shown in FIG. 3, for example, the conductive element is positioned within the ocular portion 20 such that the conductive element 38 is at least partially exposed through the first proximal surface 28a (e.g., positioned to directly or indirectly contact the cornea). In other embodiments, the conductive element 38 may be positioned such that it is at least partially exposed through the second proximal surface (e.g., positioned to directly or indirectly contact the sclera, such as shown in FIG. 4).

In embodiments wherein the ocular portion 20 includes only one conductive element, a second conductive element separate from the electroretinography device 10 is typically attached to a portion of the subject's body to serve as a reference electrode. However, in other embodiments, the ocular portion 20 includes a first conductive electrode configured to detect biopotential signals from a subject's eye and a second conductive element configured to contact a different portion of the subject's eye. As shown in FIG. 4, one such embodiment of an ocular portion 20 includes a distal surface 26, at least one side wall 22, a first proximal surface 28a configured to conform to a cornea of an eye, a second proximal surface 28b configured to conform to a sclera of the eye, a first conductive element 38 and a second conductive element 39. The first conductive element 38 is positioned within the ocular portion 20 such that at least a portion of the first conductive element 38 is exposed through the first proximal surface 28a (e.g., positioned to directly or indirectly contact the cornea). The second conductive element 39 is positioned within the ocular portion 20 such that at least a portion of the second conductive element 39 is exposed through the second proximal surface 28b (positioned to directly or indirectly contact the sclera). In one embodiment, the first conductive element 38 serves as the recording electrode (e.g., is configured to detect biopotential signals from the eye), while the second conductive element 39 serves as a reference electrode. In another embodiment, the first conductive element 38 serves as the reference electrode, while the second conductive element 39 serves as the recording electrode (e.g., is configured to detect biopotential signals from the eye).

Figure 6:
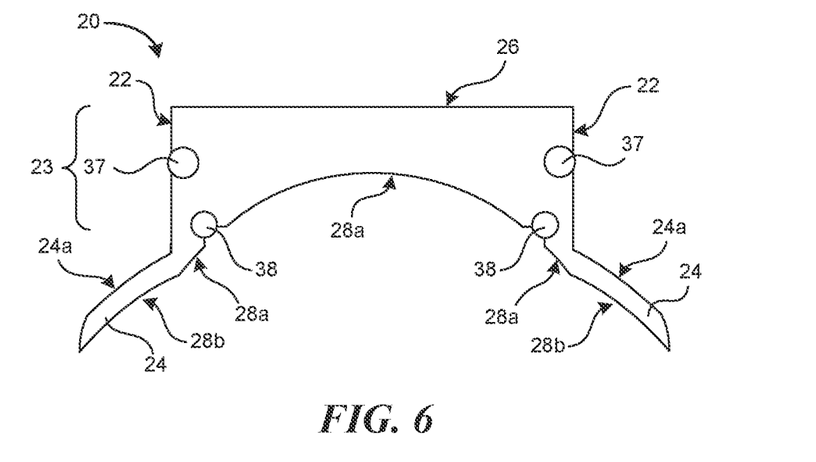
FIG. 6 is a cross sectional view through another embodiment of an electroretinography device configured in accordance with the present technology.

In some embodiments, the ocular portion 20 may include a second conductive element positioned to contact a portion of the subject that is not a portion of the anterior surface of the eye, such as one or both eyelids. For example, as shown in FIG. 6, in some embodiments the distal portion 23 includes a second conductive element 37 positioned such that at least a portion of the second conductive element 37 is exposed through the at least one side wall 22. In such embodiments, the first conductive element 38 may be positioned in any suitable location to make direct or indirect contact with the anterior surface of the eye. For example, as shown in FIG. 6, the first conductive element 38 may be positioned within the ocular portion 20 such that a portion of the first conductive element is exposed through the first proximal surface (e.g., positioned to directly or indirectly contact the cornea). In other embodiments, the first conductive element 38 is positioned within the proximal portion 24 such that at least a portion of the first conductive element 38 is exposed through the second proximal surface 28b (e.g., positioned to directly or indirectly contact the sclera).

Figure 5:
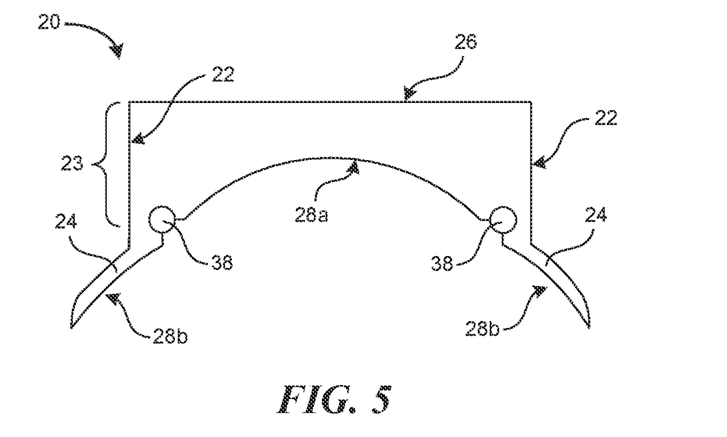
FIG. 5 is a cross sectional view through another embodiment of an electroretinography device configured in accordance with the present technology.

In some embodiments, the proximal portion 24 is configured to allow one or both eyelids to slide over the proximal portion 24. As shown in FIG. 5, for example, the proximal portion 24 may include a flange-like shape that extends outwardly from the distal portion 23. In such embodiments, the conductive element 38 can be positioned in any suitable location as described herein, including in a position such that at least a portion of the conductive element 38 is exposed through the first proximal surface 28*a* as shown in FIG. 5.

Figure 7:
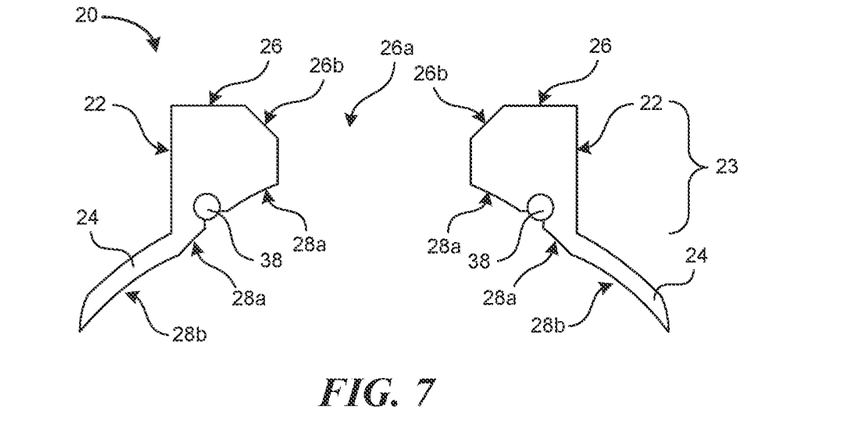
FIG. 7 is a cross sectional view through another embodiment of an electroretinography device configured in accordance with the present technology.

In some embodiments, the ocular portion 20 is configured to permit incident light to reach the anterior surface of the eye unimpeded (e.g., without first passing through any portion of the ocular portion 20). In such embodiments, the ocular portion 20 may include a void 26*a* extending through the ocular portion 20. In some embodiments, such as that shown in FIG. 7, the ocular portion 20 may include a distal portion 23 which includes a void 26*a* extending through the distal portion 23 and the proximal portion 24 (including through the first proximal surface 28*a*). In such embodiments, the distal surface 26 may include a contour 26*b* (e.g., a bevel or curve) adjacent to the void 26*a*. The first conductive element 38 can be positioned in any suitable location as described herein, including in a position such that at least a portion of the conductive element 38 is exposed through the first proximal surface 28*a* as shown in FIG. 7.

Figure 8:
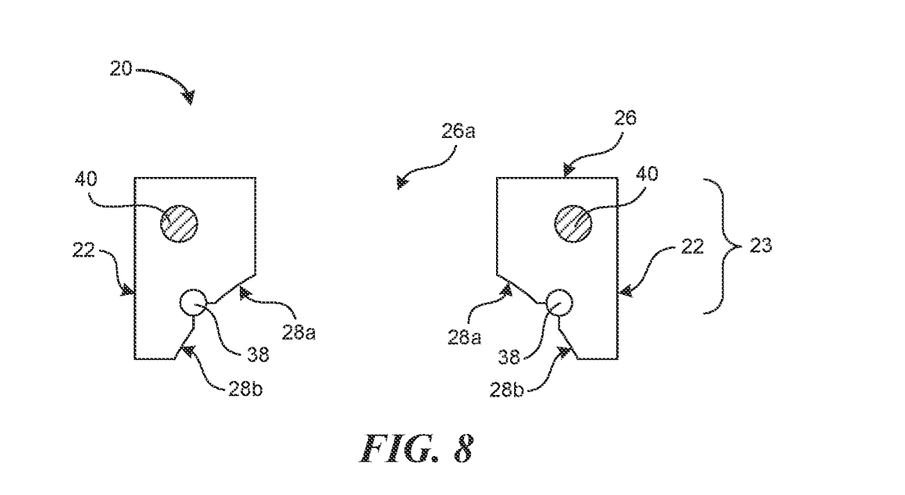
FIG. 8 is a cross sectional view through another embodiment of an electroretinography device configured in accordance with the present technology.
Figure 9:
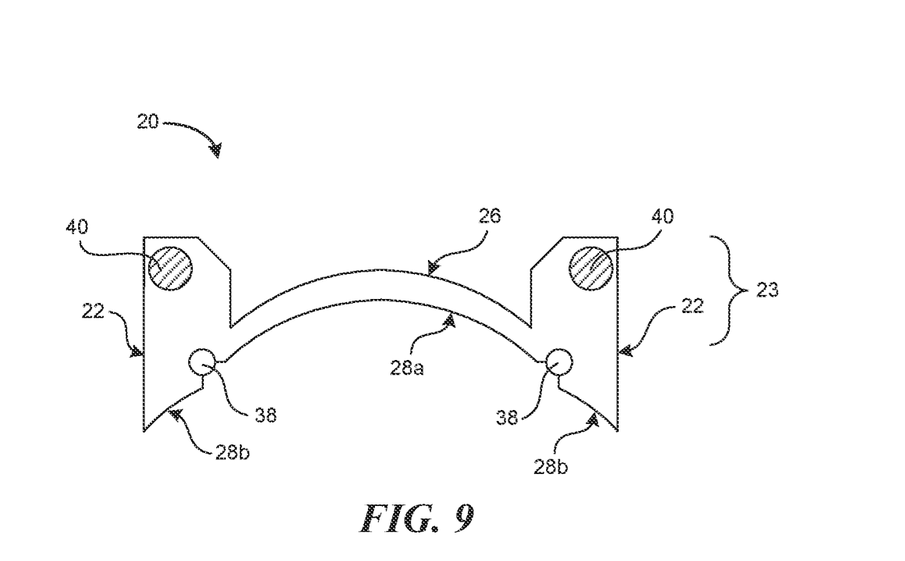
FIG. 9 is a cross sectional view through another embodiment of an electroretinography device configured in accordance with the present technology.
Figure 11:
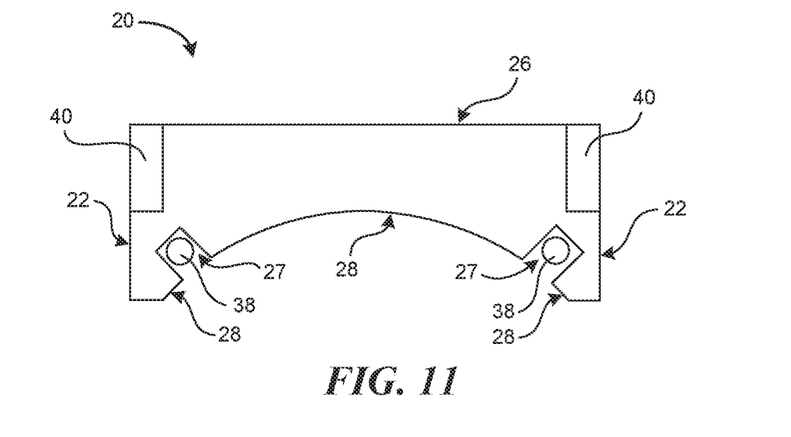
FIG. 11 is a cross sectional view through another embodiment of an electroretinography device configured in accordance with the present technology.

Referring to FIGS. 8, 9 and 11 collectively, some embodiments, particularly those including a void 26*a* through the ocular portion 20, include an ocular portion 20 that additionally includes a stabilizing element 40. The stabilizing element 40 comprises, consists essentially of, or consists of a material that is more rigid than the material used to form the remainder of the ocular portion 20. In such embodiments, the stabilizing element 40 provides increased mechanical rigidity to the ocular portion 20, for example to resist lateral forces (e.g., pressure exerted on the side wall(s) 22 by the subject's eyelids). In some embodiments, the stabilizing element 40 comprises, consists essentially of, or consists of a material having a Young's modulus of elasticity of 100 MPa or greater. In some embodiments, the stabilizing element 40 comprises, consists essentially of, or consists of a tetrafluoroethylene (e.g., TEFLON), an acetal resin (e.g., DELRIN), an acrylic (e.g., poly(methyl methacrylate)), a polycarbonate, a glass, stainless steel, or a combination thereof. The size and amount of the stabilizing element 40 to be used depends in part on the relative difference in Young's modulus values of the stabilizing element 40 and the material comprising the ocular portion 20, and in part on the shape of the ocular portion 20. In general, however, less stabilizing element 40 is required when the difference in Young's modulus values is large and when the ocular portion 20 does not include voids or other discontinuities (e.g., void 26*a*). The stabilizing element 40 can be introduced into the device before, during or after formation of the ocular portion 20. For example, in some embodiments the stabilizing element 40 is placed into a mold before the material used to form the ocular portion is added to the mold. In other embodiments, the stabilizing element 40 is added to the ocular portion 20 after a molding step.

The stabilizing element 40 may be positioned at any suitable location within the ocular portion 20, and may be configured in any suitable shape to provide rigidity to the ocular portion 20. In some embodiments, the stabilizing element 40 has a general ring shape and is positioned inside the distal portion 23 of the ocular portion 20, such as shown in FIGS. 8-9. In other embodiments, the stabilizing element 40 is at least partially exposed. For example, as shown in FIG. 11, the stabilizing element 40 may be configured as a ring positioned around the one or more side walls 22 of the ocular portion 20. In such embodiments, the stabilizing element 40 may be positioned at or near the distal surface 26, as shown in FIG. 11, or alternatively the stabilizing element 40 may be positioned such that at least a portion of the stabilizing element 40 is covered by the distal surface 26.

Referring now to FIG. 8, one embodiment of the ocular portion 20 of the present technology includes a distal portion 23 having at least one side wall 22, a distal surface 26, a void 26*a*, and a stabilizing element 40 within the distal portion 23. The ocular portion 20 further includes a conductive element 38 positioned at or near the first proximal surface 28*a* and the second proximal surface 28*b*. The stabilizing element 40 in this embodiment is generally configured as a rounded shape (e.g., a ring) that extends through all or substantially all of the ocular portion 20.

As shown in FIG. 9, another embodiment of the ocular portion 20 includes a conductive element 38 positioned at or near a first proximal surface 28*a* and/or a second proximal portion 28*b*, and a distal portion 23 having at least one side wall 22, a stabilizing element 40, and a distal surface 26 that is generally convex in shape. The stabilizing element 40 in such embodiments may be relatively larger and/or formed of a material having a relatively higher Young's modulus value than, for example, the stabilizing element 40 used in embodiments such as that shown in FIG. 8.

Referring now to FIG. 11, another embodiment of the ocular portion 20 includes a conductive element 38 positioned within one or more channels 27 formed within the proximal surface 28, a distal surface 26, and a stabilizing element 40 positioned at or near the outer edge of the side wall 22. The stabilizing element 40 may be configured to be flush with the distal surface 26, or alternatively may be configured to be covered at least partially by the distal surface 26.

Figure 12:
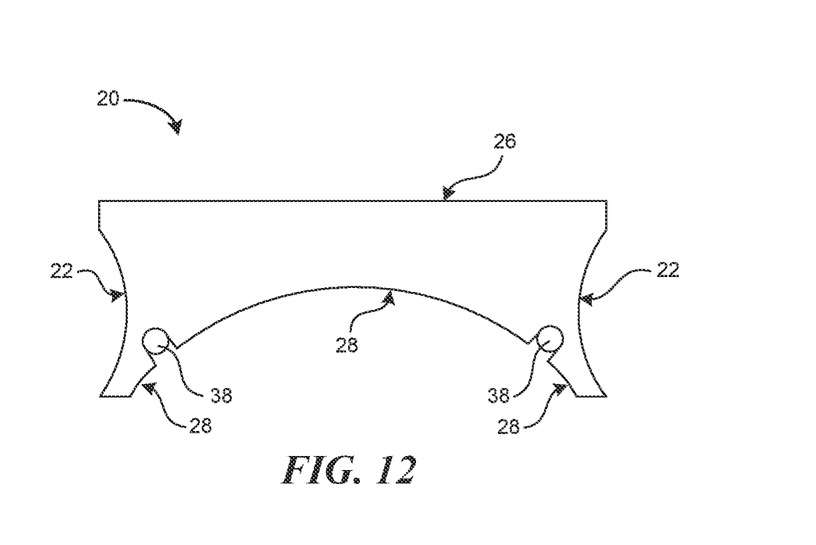
FIG. 12 is a cross sectional view through another embodiment of an electroretinography device configured in accordance with the present technology.

As shown in FIG. 12, in some embodiments the one or more side walls 22 have a contoured surface that accommodates the subject's eyelids. In such embodiments, the contoured surface may be generally concave and the side wall(s) 22 may have a height sufficient to prevent the eyelids from closing over the distal surface 26.

Figure 13:
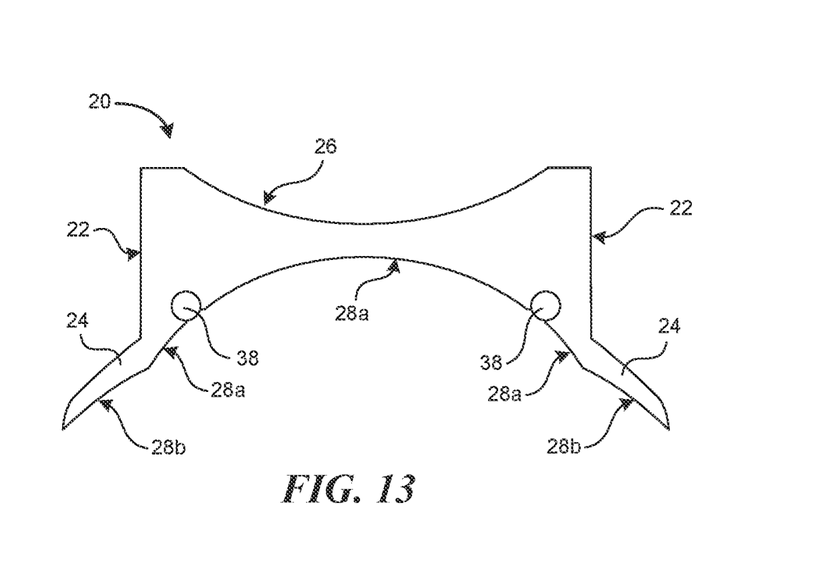
FIG. 13 is a cross sectional view through another embodiment of an electroretinography device configured in accordance with the present technology.

Referring now to FIG. 13, an ocular portion 20 of some embodiments of the present technology includes a distal surface 26 having a generally concave shape. In such embodiments, the ocular portion 20 additionally serves as a diverging lens to affect the distribution of incident light on the subject's retina. This configuration of the distal surface 26 may be used in conjunction with any other embodiment of the present technology; for example the proximal portion 24 may be configured to include a flange shape, and may include a conductive element 38 at or near a first proximal surface 28*a* configured to conform to the subject's cornea and/or a second proximal surface 28*b* configured to conform to the subject's sclera. The one or more side walls 22 may be configured to be generally straight as shown in FIG. 13, or may alternatively adopt another shape, such as generally concave as shown in FIG. 12.

Figure 14:
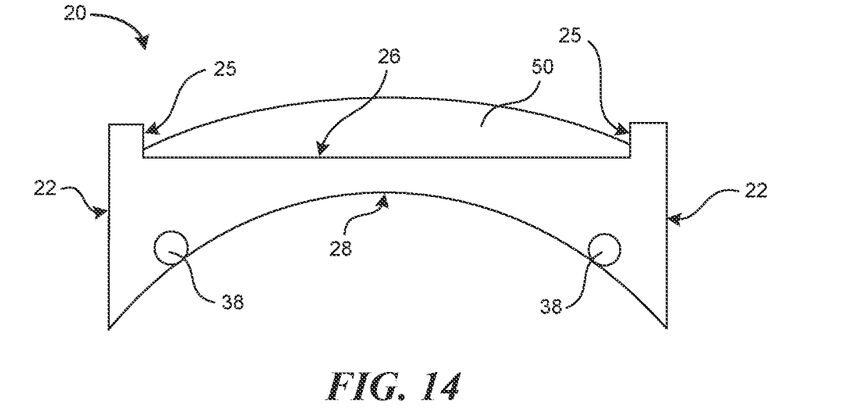
FIG. 14 is a cross sectional view through another embodiment of an electroretinography device configured in accordance with the present technology.

As shown in FIG. 14, another embodiment of the present technology provides an ocular portion 20 including a lens 50 configured, for example, to affect the subject's acuity in any desired manner. The distal surface 26 in such embodiments may include one or more retaining portions 25 configured to securely retain the lens 50. In some embodiments, the retaining portions 25 are configured to enable exchange or replacement of the lens 50 before or after the ocular portion 20 is installed on an anterior surface of the subject's eye. For example, the retaining portions 25 may be configured to be sufficiently flexible to allow a clinician to remove the lens 50 from the ocular portion 20 without exerting undue pressure or lateral force on the ocular portion 20.

Figure 15:
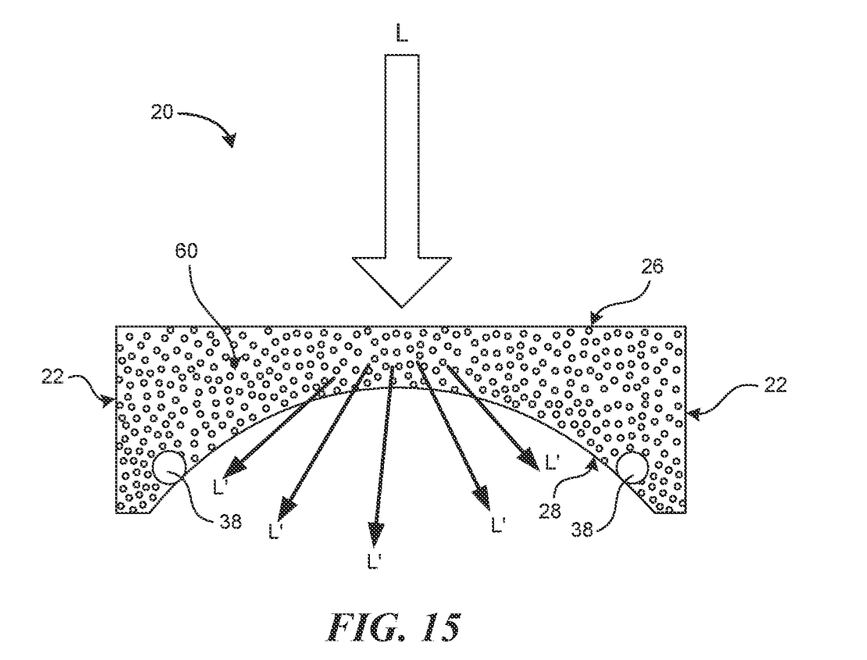
FIG. 15 is a cross sectional view through another embodiment of an electroretinography device configured in accordance with the present technology.

In some embodiments, the ocular portion 20 further includes a diffusing component which has an index of refraction different than the index of refraction of the flexible material used to form the ocular portion 20. As shown in FIG. 15, the diffusing component 60 may be dispersed evenly or substantially evenly throughout the ocular portion 20. In such embodiments, incident light L enters the ocular portion 20 through the distal surface 26 and is scattered by passing through the two materials such that the emerging light L' is scattered (e.g., diffuse). The diffusing component 60 may be incorporated into any embodiment disclosed herein. As such, the conductive element 38 may be located at any suitable location including, for example, at or near the proximal surface 28 as shown in FIG. 15.

Figure 16:
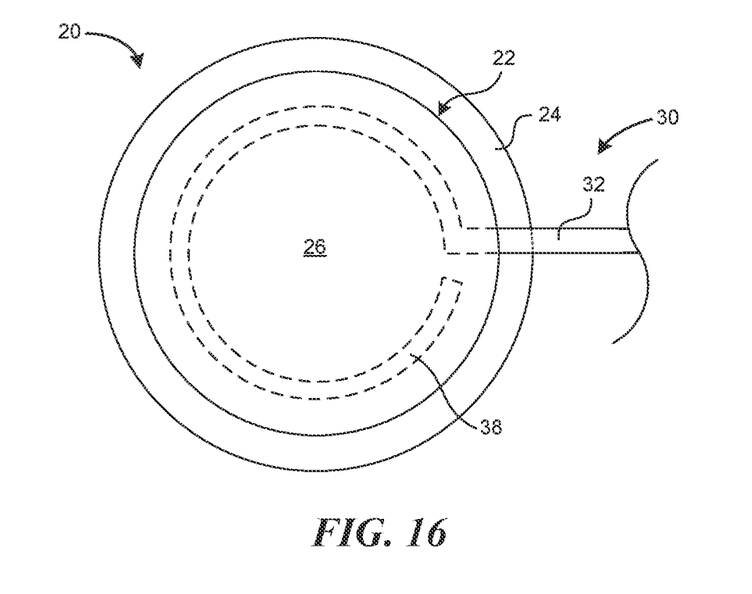
FIG. 16 is a perspective view of another embodiment of an electroretinography device configured in accordance with the present technology as viewed from above the distal surface.

As shown in FIG. 16, the conductive element 38 is operatively connected (e.g., electrically connected) to the signal relay 30, and may be protected from breakage or damage by the flexible portion 32 of the signal relay 30. The conductive element 38 may adopt a loop or partial loop shape, as shown in FIG. 16. In such embodiments, the conductive element 38 is positioned near the side wall 22 and below the distal surface 26. The proximal portion 24 extends beyond the edge of the side wall 22 to allow the subject's eye lids to slide over the proximal portion 24 and thus apply a stabilizing force to the ocular portion 20.

Figure 17:
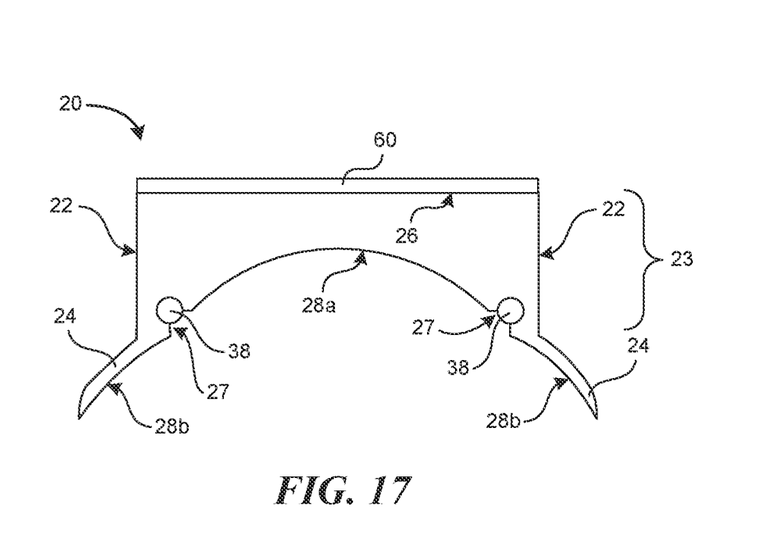
FIG. 17 is a cross sectional view through another embodiment of an electroretinography device configured in accordance with the present technology.

Referring now to FIG. 17, an ocular portion 20 of the present technology is formed of a material comprising, consisting essentially of, or consisting of a component having a Young's modulus of no more than about 50 MPa (e.g., PDMS), and includes a conductive element 38, a distal portion 23 and a proximal portion 24. The proximal portion 24 includes a first proximal surface 28a configured to conform to the cornea of a subject's eye, and a second proximal surface 28b configured to conform to the sclera of the subject's eye. The proximal portion 28 includes a flange shaped extension configured to enable the subject's eyelids to slide over the flange. The conductive element 38 is formed of a conductive material as described herein, and is positioned within a channel 27 formed in the proximal surface 28a/28b which enables the conductive element 38 to be in indirect contact with the anterior surface of the subject's eye. In such an embodiment, the biopotential signal is transmitted to the conductive element 38 through a conductive medium between the anterior surface of the eye and the conductive element 38, such as saline, natural tears, artificial tears, or a similar biocompatible and electrically conductive fluid. The distal portion 23 includes a side wall 22 that is generally perpendicular to the distal surface 26. A diffusing component 60 is positioned adjacent to the distal surface 26 and is configured to diffuse incident light. The diffusing component 60 may include a translucent material, such as a light-scattering component suspended in PDMS or another suitable substrate, that permits diffuse light to pass through the ocular portion 20 to the subject's eye. The diffusing component 60 may be applied as a coating to the distal surface 26 after formation of the remainder of the distal portion 23, or may be formed integrally with the ocular portion 20 along with the remainder of the distal portion 23.

Figure 10:
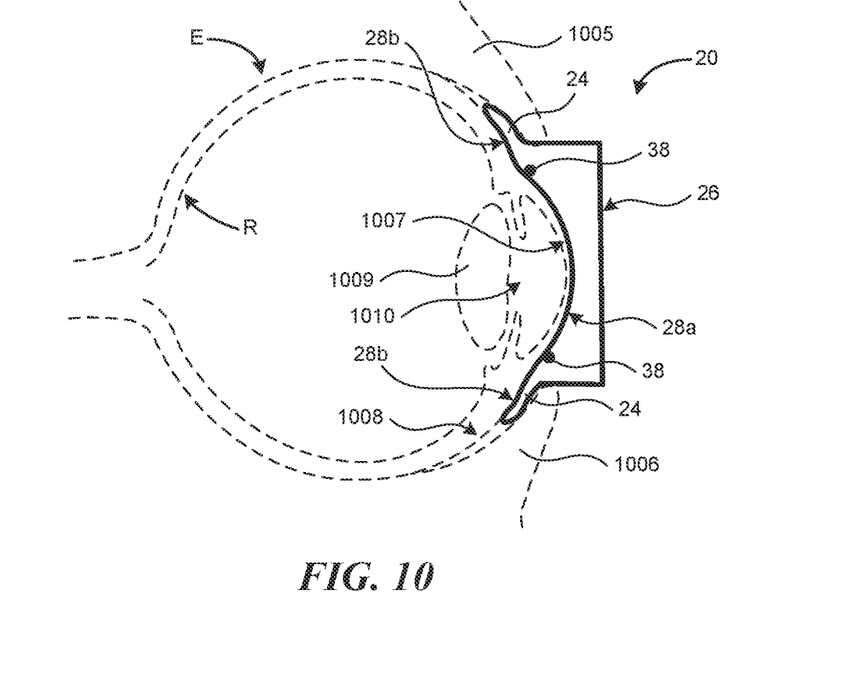
FIG. 10 is a cross sectional view through another embodiment of an electroretinography device configured in accordance with the present technology and positioned in contact with the anterior surface of a subject's eye.

Referring now to FIG. 10, an ocular portion 20 consistent with the present technology is positioned on the anterior surface of a subject's eye E. In some embodiments, the ocular device 20 is positioned such that a first distal surface 28a conforms to and contacts the cornea 1007, while a second proximal surface 28b conforms to and contacts the sclera 1008. The upper eyelid 1005 and lower eyelid 1006 help retain the ocular portion 20 against the cornea 1007 and the sclera 1008 by, for example, applying pressure against the flange-shaped portion of the distal portion 24. In such a configuration, the distal surface 26 is generally tangential to the cornea 1007, such that incident light can pass through the ocular portion 20 through the pupil 1010 and lens 1009 to the retina R. Biopotential signals produced by the illuminated retina R are then detectable by the conductive element 38, which is positioned in direct or indirect contact with the anterior surface of the eye E.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. While advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown or described herein.

The invention claimed is:

1. An ocular device configured to detect one or more biopotential signals from a patient, the ocular device comprising:
    an ocular region configured to be placed in contact with an anterior surface of an eye, wherein the ocular region is monolithic such that a continuous surface extends along an entirety of the ocular region, the ocular region comprising—
        a distal portion including an outermost sidewall; and
        a proximal portion coupled to the distal portion and including a flange region extending from the sidewall of the distal portion in a radially outward direction, the flange region including (i) an inner surface that is a proximal-most surface of the ocular region and (ii) an outer surface configured to abut an eyelid of the patient when the device is disposed over the eye; and
        a void between the outermost sidewall of the distal portion, wherein the void extends (i) across the ocular region and (ii) through the proximal portion and the distal portion,
        wherein:
            the inner surface includes (i) a first region extending laterally inward and partially distally, and (ii) a second region, laterally inward of the first region, extending laterally inward and partially distally further, and
            when the device is disposed over the eye, the first region is positioned over a portion of a sclera of the patient and the second region is positioned over a portion of the cornea of the patient; and
        a conductor disposed within the ocular region and configured to be operatively connected to a signal relay.

2. The ocular device of claim 1, wherein the distal portion has a first maximum cross-sectional dimension and the proximal portion has a second maximum cross-sectional dimension greater than the first maximum cross-sectional dimension.

3. The ocular device of claim 1, wherein, when the device is disposed over the eye, the distal portion is configured to inhibit the eyelid from blocking light received by the eye.

4. The ocular device of claim 1, wherein the conductor is disposed within the ocular region such that a portion of the conductor is exposed, and wherein, when the device is disposed over the eye, the conductor is spaced apart from the anterior surface of the eye.

5. The ocular device of claim 1, wherein the conductor consists of a conductive element having a partially circular or oval shape.

6. The ocular device of claim 1, wherein the flange region extends from the sidewall of the distal portion such that a cross-sectional dimension of the flange region within the proximal portion decreases in a distal direction.

7. The ocular device of claim 1, wherein the void includes a first cross-sectional dimension within the distal portion and a second cross-sectional dimension within the proximal portion, the second cross-sectional dimension being greater than the first cross-sectional dimension.

8. The ocular device of claim 7, wherein the first cross-sectional dimension is constant in the distal region and the second cross-sectional dimension varies in the proximal region.

9. The ocular device of claim 7, wherein the first cross-sectional dimension is constant in the distal region and the second cross-sectional dimension increases in a proximal direction.

10. The ocular device of claim 1, wherein the first region has a first radius of curvature and the second region has a second radius of curvature different than the first radius of curvature, and wherein the conductor is disposed at the second region.

11. The ocular device of claim 1, wherein, when the device is disposed over the eye, the conductor is disposed over a portion of the cornea of the patient.

12. The ocular device of claim 1, wherein the void is defined by inner sidewalls that are straight and extend along an axis away from the proximal region.

* * * * *

UNITED STATES PATENT AND TRADEMARK OFFICE
CERTIFICATE OF CORRECTION

PATENT NO. : 11,766,208 B2
APPLICATION NO. : 17/188130
DATED : September 26, 2023
INVENTOR(S) : John R. Hetling et al.

It is certified that error appears in the above-identified patent and that said Letters Patent is hereby corrected as shown below:

In the Claims

In Column 10, Claim 1, Line 60, delete "the cornea" and replace with "a cornea".

In Column 12, Claim 8, Line 2 and Line 4, delete the word "region" and replace with "portion".

In Column 12, Claim 9, Line 6, delete "region" and replace with "portion".

In Column 12, Claim 12, Line 19, delete "region" and replace with "portion".

Signed and Sealed this
Twenty-eighth Day of November, 2023

Katherine Kelly Vidal
*Director of the United States Patent and Trademark Office*